United States Patent
Kaiser

(10) Patent No.: US 9,132,549 B2
(45) Date of Patent: Sep. 15, 2015

(54) METHOD AND ARRANGEMENT FOR MONITORING MOTORIZED EQUIPMENT COMPONENTS

(75) Inventor: Joachim Kaiser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 175 days.

(21) Appl. No.: 13/303,846

(22) Filed: Nov. 23, 2011

(65) Prior Publication Data
US 2012/0297872 A1 Nov. 29, 2012

(30) Foreign Application Priority Data
Nov. 25, 2010 (DE) .......................... 10 2010 061 949

(51) Int. Cl.
| | |
|---|---|
| *G01N 3/56* | (2006.01) |
| *B25J 9/16* | (2006.01) |
| *G05B 19/406* | (2006.01) |
| *A61B 6/00* | (2006.01) |

(52) U.S. Cl.
CPC ............ *B25J 9/1674* (2013.01); *A61B 6/4458* (2013.01); *G05B 19/406* (2013.01); *G05B 2219/40549* (2013.01); *G05B 2219/42314* (2013.01); *G05B 2219/43021* (2013.01); *G05B 2219/45169* (2013.01); *G05B 2219/50197* (2013.01)

(58) Field of Classification Search
None
See application file for complete search history.

(56) References Cited

U.S. PATENT DOCUMENTS

| | | | | |
|---|---|---|---|---|
| 6,598,456 | B2 * | 7/2003 | Potts .......................... | 73/12.07 |
| 7,305,863 | B2 * | 12/2007 | Recknagel et al. ............ | 73/1.38 |
| 7,661,291 | B2 * | 2/2010 | McMahan et al. ............. | 73/1.38 |
| 7,715,992 | B2 | 5/2010 | Kashio et al. | |
| 8,042,377 | B2 * | 10/2011 | Froman et al. .................. | 73/1.37 |
| 8,190,294 | B2 | 5/2012 | Sjostrand et al. | |
| 2005/0131602 | A1 * | 6/2005 | Souda ............................. | 701/34 |
| 2007/0028664 | A1 * | 2/2007 | Ukai .............................. | 73/1.37 |
| 2008/0174444 | A1 * | 7/2008 | Noda et al. .................... | 340/669 |
| 2009/0028290 | A1 | 1/2009 | Grebner et al. | |

FOREIGN PATENT DOCUMENTS

| | | |
|---|---|---|
| CN | 101116042 A | 1/2008 |
| CN | 101259615 A | 9/2008 |
| DE | 10 2007 033 716 A1 | 1/2009 |
| DE | 10 2008 021 671 A1 | 11/2009 |

(Continued)

OTHER PUBLICATIONS

German Office Action dated Jul. 11, 2011 for corresponding German Patent Application No. DE 10 2010 061 949.3 with English translation.

(Continued)

*Primary Examiner* — Robert R Raevis
(74) *Attorney, Agent, or Firm* — Lempia Summerfield Katz LLC

(57) ABSTRACT

A method for monitoring motorized equipment components includes determining first acceleration values of at least one equipment component during an encoded presettable motion sequence of the at least one equipment component at a first time point. The method also includes determining second acceleration values of the at least one equipment component during the encoded presettable motion sequence of the at least one equipment component at a second time point. The method includes emitting an error signal when a presettable number of the second acceleration values lies outside a presettable tolerance range of the first acceleration values.

20 Claims, 4 Drawing Sheets

(56) References Cited

FOREIGN PATENT DOCUMENTS

| | | |
|---|---|---|
| DE | 10 2008 054 312 A1 | 5/2010 |
| EP | 1 724 072 A1 | 11/2006 |

OTHER PUBLICATIONS

Chinese Office Action for related Chinese Application No. 201110335852.2, mailed Mar. 31, 2015, with English Translation.

* cited by examiner

METHOD AND ARRANGEMENT FOR MONITORING MOTORIZED EQUIPMENT COMPONENTS

This application claims the benefit of DE 10 2010 061 949.3, filed on Nov. 25, 2010.

BACKGROUND

The present embodiments relate to a method and an arrangement for monitoring motorized equipment components by determining acceleration values.

FIG. 1 shows, as an example of equipment according to the prior art, a perspective view of a known C-arm 7 arranged on a robot with six axes of rotation. A carousel 2 that may be rotated about a first axis of rotation is supported on a base frame 1 that, for example, is permanently mounted on a floor. A swinging bracket 3 that may be swiveled about a second axis of rotation is attached to the carousel 2. An arm 4 that may be rotated about a third axis of rotation is fixed to the swinging bracket 3. A hand 5 that may be rotated about a fourth axis of rotation is arranged at an end of the arm 4. The hand 5 has a retaining element 6 that may be rotated about an axis of rotation and may be swiveled about a fifth axis of rotation running perpendicular thereto. The C-arm 7 is coupled to the retaining element 6 of the hand 5. An X-ray detector 8 is attached at a first end of the C-arm 7 and an X-ray source 9 in an opposing arrangement at a second end.

When this C-arm arrangement has been in operation for a number of years, wear and tear to gear mechanisms, bearings, brakes or toothed belts may jeopardize the accuracy of a position setting as well as reliability of operation.

In the case of non-medical robot equipment, an occurrence of inaccuracies in the motion sequences of the motorized equipment components results in inaccuracies in the motion sequences or activities executed with the robot arms or moving axes. The consequence may be inaccurate welding seams, for example.

SUMMARY AND DESCRIPTION

The present embodiments may obviate one or more of the drawbacks or limitations in the related art. For example, a method and an arrangement that identify inaccuracies in motion sequences of motorized equipment components may be provided.

In the present embodiments, accelerations are measured in order to monitor moving equipment components. Acceleration may refer to any change in a velocity vector (e.g., including a decrease in the absolute value or also a change in direction at a constant velocity value). The acceleration is the time derivative of the velocity vector or the second time derivative of the position vector.

In addition to linear acceleration, there is also angular acceleration. Angular acceleration refers to the change over time in the angular velocity of a rotating object. In mathematical terms, the angular acceleration is the derivative of the angular velocity with time.

The present embodiments include a method for monitoring motorized equipment components (e.g., equipment components of a robot) with the acts of: determination of first acceleration values of at least one equipment component during a presettable motion sequence of the equipment components at a first point in time; determination of second acceleration values of the equipment component during the presettable motion sequence of the equipment components at a second point in time; and emission of an error signal, if a presettable number of the second acceleration values lies outside a presettable tolerance range of the first acceleration values. The present embodiments offer the advantage that deviances in motion sequences of equipment components caused by wear and tear to mechanical components (e.g., undesired vibrations) may be identified at an early stage and appropriate service measures may be taken in good time.

In one embodiment of the method, the tolerance range may be determined from a repeated determination of the first acceleration values (e.g., by statistical methods). As a result, tolerance-related deviances are taken into account.

In another embodiment of the method, the tolerance range may be formed by maximum and minimum first acceleration values.

The first and second acceleration values may include linear accelerations and/or angular accelerations.

In another embodiment of the method, the first and second acceleration values may be determined simultaneously at multiple equipment components.

In one embodiment, equipment parameters may additionally be captured during the determination of the first and second acceleration values.

The equipment parameters may include motor currents and/or speed sensor signals.

The present embodiments also include an arrangement for monitoring motorized equipment components with at least one acceleration sensor arranged at an equipment component. The arrangement determines first acceleration values at a first point in time and second acceleration values at a second point in time with an acquisition unit that may exchange data with the acceleration sensor and may emit an error signal if a presettable number of the second acceleration values lies outside a presettable tolerance range of the first acceleration values.

In one embodiment, the acquisition unit may determine the tolerance range from a repeated determination of the first acceleration values using, for example, statistical methods.

In another embodiment, the acquisition unit may form the tolerance range using maximum and minimum first acceleration values.

In the arrangement, the first and second acceleration values may include linear accelerations and/or angular accelerations. In one embodiment, the first acceleration values and the second acceleration values include linear accelerations, angular accelerations, both position values static over time and dynamic acceleration values, or a combination thereof.

In one embodiment, the acceleration sensors may be arranged at different equipment components in the arrangement.

In another embodiment, the acceleration sensor may include a data acquisition unit, an evaluation unit and a communication unit. As a result, the measured acceleration values may be saved and checked, a result of the check displayed, a response given to external signals, signals passed to external units, and data exchanged with external units (e.g., acquisition or control units).

In one embodiment, the arrangement may include a control unit that controls the motion of the equipment components and is electrically or electromagnetically connected to the acquisition unit.

The arrangement may include an X-ray C-arm.

Other particularities and advantages of the present embodiments emerge from the following explanations of several exemplary embodiments on the basis of schematic drawings.

DETAILED DESCRIPTION OF THE DRAWINGS

Figure 1:
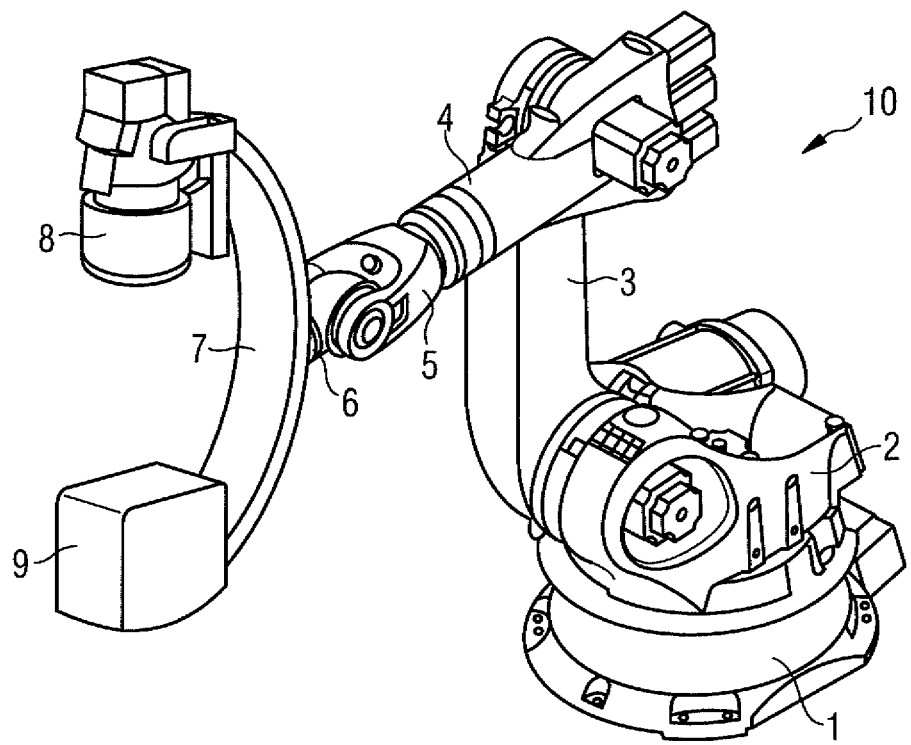
FIG. 1 shows a perspective view of a C-arm of the prior art arranged on a robot.
Figure 2:
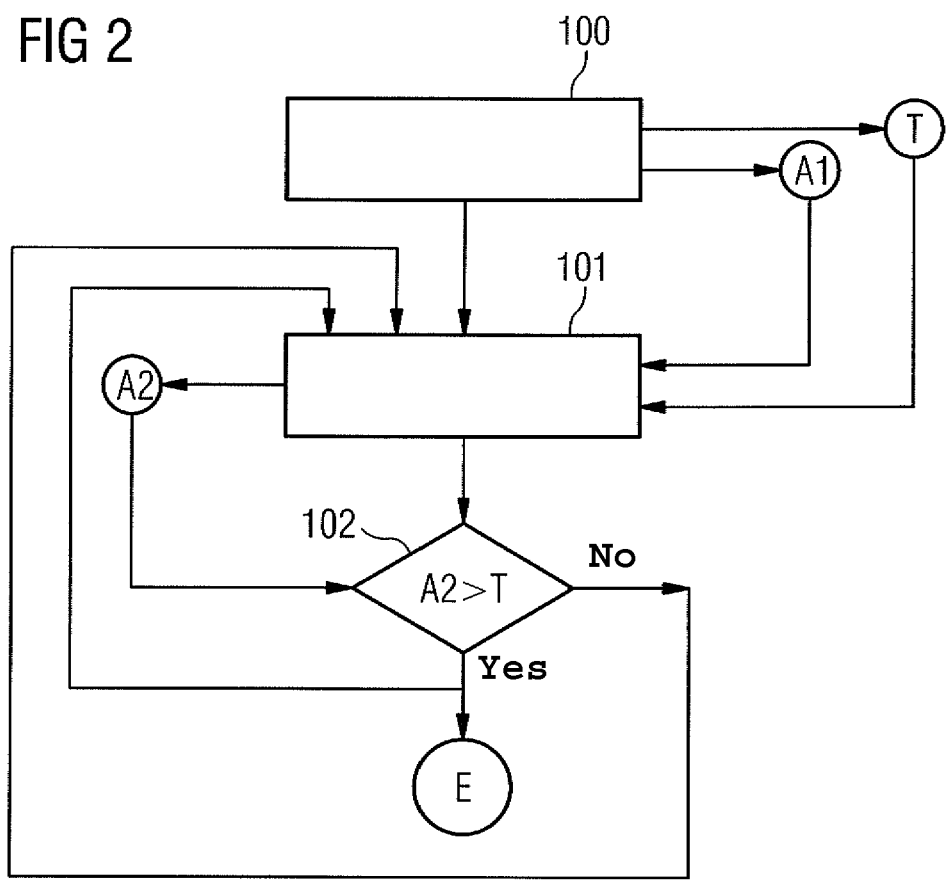
FIG. 2 shows a flow chart of one embodiment of a method for monitoring motorized equipment components.
Figure 3:
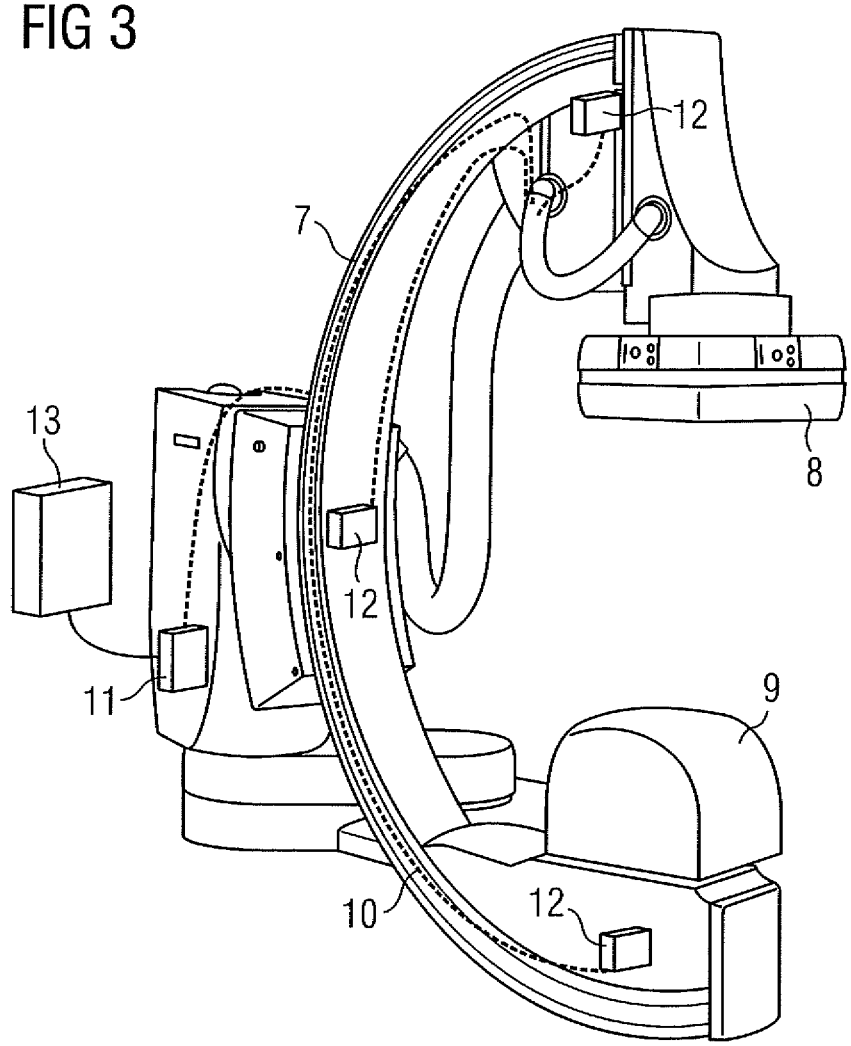
FIG. 3 shows one embodiment of a C-arm arrangement with monitoring of motorized equipment components.

FIG. 2 shows a flow chart of one embodiment of a method for monitoring motorized equipment components. In an initialization phase 100, a motion cycle of the movable equipment components of, for example, a C-arm arrangement according to FIG. 3 is performed at a first point in time (e.g., a first time point). The motion cycle includes a sequence of different, presettable and appropriately encoded motion sequences of the equipment components (e.g., partial cycles). Individual axes of the equipment components are moved separately or synchronously. Several of the motion cycles are similarly performed repeatedly with identical equipment parameters. In all motion cycles, first acceleration values A1 are determined. Permissible tolerance ranges T for the first acceleration values A1 for each partial cycle are determined from the measured first acceleration values A1. For example, the tolerance range T is provided as a result of a determined maximum of the first acceleration values A1.

In a test phase 101, the motion cycle is executed as a whole or as individual partial cycles at a second point in time (e.g., a second time point). The second time point lies after the initialization phase 100. Second acceleration values A2 are determined and compared with the determined (e.g., saved) tolerance ranges T for each partial cycle. If a presettable number of the second acceleration values A2 lies outside the tolerance ranges T, an impermissible deviance in the motion sequences may be inferred, and in act 102, a corresponding error signal E is emitted. Based on the error signal E, a defective drive or gear mechanism may be identified, for example, and appropriate service measures initiated.

Alternatively, in normal operation of the equipment, the second acceleration values A2 may be determined. If a motion sequence matches a stored partial cycle, the monitoring of the tolerance range T is performed. A separate test phase may thereby be avoided.

FIG. 3 shows a perspective view of a C-arm arrangement with monitoring of motorized equipment components. FIG. 3 shows a C-arm 7. An X-ray source 9 is attached to one end of the C-arm 7, and an X-ray detector 8 is attached to another end of the C-arm 7. Acceleration sensors 12 are arranged on the C-arm 7 (e.g., three acceleration sensors 12: two acceleration sensors 12 at ends of the C-ram and one sensor 12 in an angle bisector). The three acceleration sensors 12 are electrically connected to an acquisition unit 11 via connection lines 10. In the event of motions of the C-arm 7, the acceleration sensors 12 measure second acceleration values A2 that are passed to the acquisition unit 11.

In another advantageous embodiment, acceleration sensors 12 are arranged on the C-arm 7; the acceleration sensors 12 initially buffer the first acceleration values A1 and the second acceleration values A2 and once the motion of the C-arm has ceased, pass the first acceleration values A1 and the second acceleration values A2 to another acquisition unit 11.

The second acceleration values A2 are compared with a previously determined tolerance range T at the other acquisition unit 11. If a presettable number of second acceleration values A2 lies outside the previously determined tolerance range T, an error signal is emitted. The acquisition unit 11 is connected to a control unit 13 that controls the motion of the C-arm 7.

In another advantageous embodiment, the permitted tolerance ranges are held directly on the acceleration sensor and are compared with the measured data from the acceleration sensors depending on the encoding of the motion sequence. A signal and/or data may be passed to the acquisition unit 11 via the communication unit of the acceleration sensor.

The tolerance range T is determined in an initialization phase when the C-arm equipment is erected. According to the explanations relating to FIG. 2, test motion cycles of the C-arm 7 are traversed, and first acceleration values A1 are measured. Maximum first acceleration values A1 occurring, for example, produce the tolerance range T for each associated motion cycle. Alternatively, the tolerance ranges may be determined from the first acceleration values A1 by suitable mathematical algorithms, whereby mathematical functions (e.g., for noise reduction, smoothing, and/or averaging) and, for example, statistical methods may be applied for the determination.

The sequence of the motion sequences and the parameters for motor control of the C-arm 7 required for the sequence are saved in the control unit 13. In the initialization phase 100 and in the test phase 101 according to FIG. 2, a code for a subsequent motion sequence is sent from the control unit 13 to the acquisition unit 11. As a result, in the initialization phase 100, the recording of measured acceleration values may be organized, and the determination of the permitted tolerance ranges T for each encoded motion sequence may be performed. In the test phase 101, the appropriate set of tolerance range data may thus be selected. The comparison of the tolerance range data with the currently captured second acceleration values A2 may be performed either in the acquisition unit 11 or directly in the acceleration sensors 12. A violation of the tolerance range T is sent to the control unit 13 of the C-arm with the code of the motion sequence, where the violation is, for example, captured in an error report.

During the motion cycle, other equipment parameters such as motor currents and speed sensor signals may also be recorded and incorporated into the tolerance range model.

Figure 4:
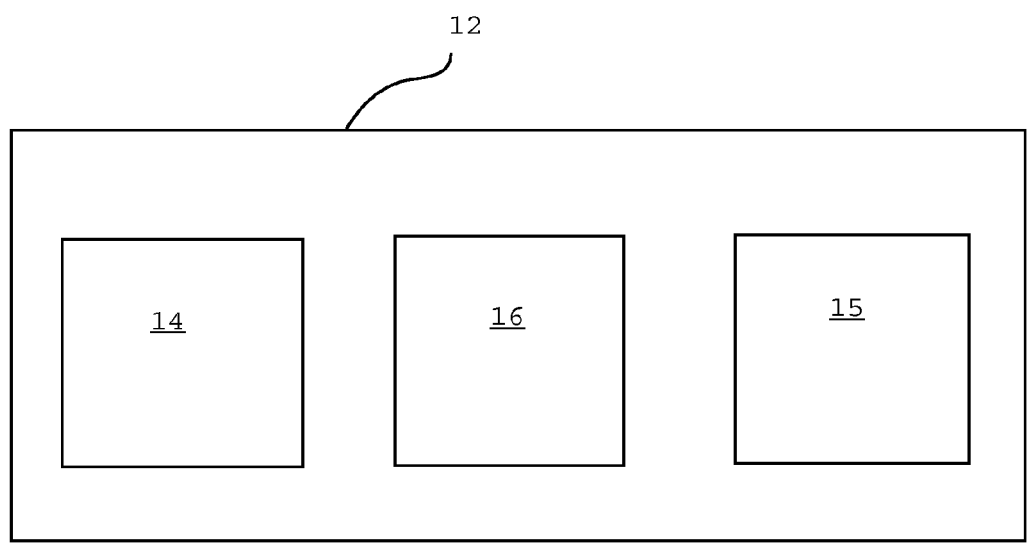
FIG. 4 shows one embodiment of an acceleration sensor that includes a data acquisition unit, a communication unit, and an evaluation unit.

The acceleration sensors 12 are designed such that the acceleration sensors 12 capture linear accelerations and/or angular accelerations in three different directions. The acceleration sensors 12 are situated together with a data acquisition unit (not shown) and an evaluation unit (not shown) on a subassembly. FIG. 4 shows an acceleration sensor 12 that includes a data acquisition unit 14, a communication unit 16 and an evaluation unit 15. The acceleration sensors 12 also include a communication module not shown in FIG. 3 for exchanging data with the acquisition unit 11.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring a motorized equipment component, the method comprising:
determining a first acceleration value of an equipment component during an encoded motion sequence of the equipment component at a first time point;

determining a second acceleration value of the equipment component during the encoded motion sequence of the equipment component at a second time point; and emitting an error signal when a number of second acceleration values lies outside a range determined from a plurality of first acceleration values obtained by repeatedly running the encoded motion sequence.

2. The method as claimed in claim 1, wherein the first acceleration value comprises an angular acceleration.

3. The method as claimed in claim 1, wherein the second acceleration value comprises a linear acceleration.

4. The method as claimed in claim 1, wherein the second acceleration value comprises an angular acceleration.

5. The method as claimed in claim 1, wherein the range is from a minimum of the first acceleration values to a maximum of the first acceleration values.

6. The method as claimed in claim 1, wherein the first acceleration value comprises a linear acceleration.

7. The method as claimed in claim 1, further comprising:
determining a respective first acceleration value at each equipment component of a plurality of different equipment components at the first time point; and
determining a respective second acceleration value at each equipment component of the plurality of different equipment components at the second time point.

8. The method as claimed in claim 1, wherein additional equipment parameters are captured during the determination of the first acceleration value and the second acceleration value.

9. The method as claimed in claim 8, wherein the additional equipment parameters comprise motor currents, speed sensor signals, or the motor currents and the speed sensor signals.

10. The method as claimed in claim 8, wherein different motion sequences are encoded depending on a type of the encoded motion sequence.

11. An arrangement for monitoring a motorized equipment component, the arrangement comprising:
an acceleration sensor arranged at an equipment component, the acceleration sensor configured to determine a first acceleration value at a first time point and a second acceleration value at a second time point; and
an acquisition unit coupled with the acceleration sensor and configured to emit an error signal when a number of second acceleration values lies outside a range determined by the acquisition unit,
wherein data used for the determination of the range comprises a plurality of first acceleration values obtained by repeatedly running a motion sequence and encoded depending on a type of the motion sequence.

12. The arrangement as claimed in claim 11, wherein the first acceleration value comprises an angular acceleration.

13. The arrangement as claimed in claim 11, wherein the second acceleration value comprises a linear acceleration.

14. The arrangement as claimed in claim 11, wherein the second acceleration value comprises an angular acceleration.

15. The arrangement as claimed in claim 11, wherein the first acceleration value comprises a linear acceleration.

16. The arrangement as claimed in claim 11, further comprising at least one additional acceleration sensor arranged at a different equipment component for monitoring the motorized equipment component.

17. The arrangement as claimed in claim 11, wherein the acceleration sensor comprises a data acquisition unit, an evaluation unit and a communication unit.

18. The arrangement as claimed in claim 11, further comprising a control unit configured to control motion of the equipment component, the control unit being electrically or electromagnetically connected to the acquisition unit.

19. The arrangement as claimed in claim 11, further comprising an X-ray C-arm, the acceleration sensor being arranged on the X-ray C-arm.

20. The arrangement as claimed in claim 11, wherein the acquisition unit is configured to form the range from a minimum of the first acceleration values to a maximum of the first acceleration values.

* * * * *